United States Patent
van den Elzen et al.

(10) Patent No.: US 7,608,246 B2
(45) Date of Patent: Oct. 27, 2009

(54) APOLIPOPROTEIN E AS AN ADJUVANT FOR LIPID ANTIGENS

(75) Inventors: Peter van den Elzen, Vancouver (CA); Michael B. Brenner, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 11/516,017

(22) Filed: Sep. 5, 2006

(65) Prior Publication Data

US 2007/0110770 A1     May 17, 2007

Related U.S. Application Data

(60) Provisional application No. 60/713,364, filed on Sep. 2, 2005.

(51) Int. Cl.
*A61K 49/00* (2006.01)
*C12Q 1/00* (2006.01)
*G01N 33/53* (2006.01)

(52) U.S. Cl. .............. 424/9.2; 424/9.1; 424/130.1; 424/184.1; 424/234.1; 424/248.1; 424/283.1; 435/4; 435/7.1

(58) Field of Classification Search .......... 424/9.1, 424/9.2, 184.1, 234.1, 248.1, 278.1, 283.1, 424/130.1; 435/4, 7.1
See application file for complete search history.

(56) References Cited

U.S. PATENT DOCUMENTS

| | | | |
|---|---|---|---|
| 4,816,446 | A | 3/1989 | Feller et al. |
| 5,010,063 | A | 4/1991 | Piani et al. |
| 5,039,529 | A | 8/1991 | Bergendal et al. |
| 5,679,347 | A | 10/1997 | Porcelli et al. |
| 5,853,737 | A | 12/1998 | Modlin et al. |
| 6,238,676 | B1 | 5/2001 | Porcelli et al. |
| 6,326,476 | B1 | 12/2001 | Mattsson et al. |
| 6,953,625 | B2 | 10/2005 | Koullick et al. |
| 6,969,705 | B2 | 11/2005 | Pecquet et al. |
| 7,063,844 | B2 | 6/2006 | Porcelli et al. |

OTHER PUBLICATIONS

GenBank Submission; NIH/NCBI; Accession No. AF261279 and AF261279.1 (PRI Oct. 27, 2000).
GenBank Submission; NIH/NCBI; Accession No. AAA56833 and AAA56833.1 (PRI Nov. 30, 1994).
Barak et al., Fluorescent low density lipoprotein for observation of dynamics of individual receptor complexes on cultured human fibroblasts. J Cell Bio. Sep. 1981;90(3):595-604.
Basu et al., CD91 is a common receptor for heat shock proteins gp96, hsp90, hsp70, and calreticulin. Immunity. Mar. 2001;14(3):303-13.
Beatty et al., Trafficking and release of mycobacterial lipids from infected macrophages. Traffic. Mar. 2000;1(3):235-47.
Beisiegel et al., The LDL-receptor-related protein, LRP, is an apolipoprotein E-binding protein. Nature. Sep. 14, 1989;341(6238):162-4. Abstract Only.
Boullier et al., Scavenger receptors, oxidized LDL, and atherosclerosis. Ann N Y Acad Sci. Dec. 2001;947:214-22; discussion 222-3. Abstract Only.
Brigl et al., CD1: antigen presentation and T cell function. Annu Rev Immunol. 2004;22:817-90. Abstract Only.
Chaussabel et al., Unique gene expression profiles of human macrophages and dendritic cells to phylogenetically distinct parasites. Blood. Jul. 15, 2003;102(2):672-81.
Fazekas et al., Apolipoprotein E epsilon 4 is associated with rapid progression of multiple sclerosis. Neurology. Sep. 11, 2001;57(5):853-7. Abstract Only.
Heeren et al., Intracellular metabolism of triglyceride-rich lipoproteins. Curr Opin Lipidol. Jun. 2001;12(3):255-60. Abstract Only.
Heeren et al., Recycling of apoprotein E is associated with cholesterol efflux and high density lipoprotein internalizaiton. J Biol Chem. Apr. 18, 2003;278(16):14370-8.
Kang et al., Saposins facilitate CD1d-restricted presentation of an exogenous lipid antigen to T cells. Nat Immunol. Feb. 2004;5(2):175-81. Abstract Only.
Krul et al., Roles of apolipoproteins B and E in the cellular binding of very low density lipoproteins. J Clin Invest. Feb. 1985;75(2):361-9.
Le Naour et al., Profiling changes in gene expression during differentiation and maturation of monocyte-derived dendritic cells using both oligonucleotide microarrays and proteomics. J Biol Chem. May 25, 2001;276(21):17920-31.
Mahley et al., Apolipoprotein E: far more than a lipid transport protein. Annu Rev Genomics Hum Genet. 2000;1:507-37. Abstract Only.
Mahley et al., Apolipoprotein E: cholesterol transport protein with expanding role in cell biology. Science. Apr. 29, 1988;240(4852):622-30. Abstract Only.

(Continued)

*Primary Examiner*—Rodney P. Swartz
(74) *Attorney, Agent, or Firm*—Wolf, Greenfield & Sacks, P.C.

(57) ABSTRACT

The present invention is directed to pharmaceutical compositions that contain a combination of apolipoprotein E and an antigenic lipid. The compositions may be administered to a subject for the purpose of inducing an immune response against the lipid and in immunization protocols.

1 Claim, 6 Drawing Sheets

OTHER PUBLICATIONS

Major et al., Quantitative and qualitative differences in proatherogenic NKT cells in apolipoprotein E-deficient mice. Arterioscler Thromb Vasc Biol. Dec. 2004;24(12):2351-7.

Matsunaga et al., Mycobacterium tuberculosis pks12 produces a novel polyketide presented by CD1c to T cells. J Exp Med. Dec. 20, 2004;200(12):1559-69.

Nickerson et al., Sequence diversity and large-scale typing of SNPs in the human apolipoprotein E gene. Genome Res. Oct. 2000;10(10):1532-45.

Paik et al., Nucleotide sequence and structure of the human apolipoprotein E gene. Proc. Natl Acad Sci U S A. May 1985;82(10):3445-9.

Prigozy et al., Glycolipid antigen processing for presentation by CD1d molecules. Science. Jan. 26, 2001;291(5504):664-7. Abstract Only.

Prigozy et al., the mannose receptor delivers lipoglycan antigens to endosomes for presentation to T cells by CD1b molecules. Immunity. Feb. 1997;6(2):187-97. Abstract Only.

Rebbaa et al., Distribution of exogenously added gangliosides in serum proteins depends on the relative affinity of albumin and lipoproteins. J Lipid Res. Mar. 1995;36(3):564-72.

Sacks et al., The influence of apolipoprotein E on the interaction between normal human very low density lipoproteins and U937 human macrophages: heterogeneity among persons. Vasc Med. 1996;1(1):9-18. Abstract Only.

Shamshiev et al., Self glycolipids as T-cell autoantigens. Eur J Immunol. May 1999;29(5):1667-75. Abstract Only.

Südhof et al., The LDL receptor gene: a mosaic of exons shared with different proteins. Science. May 17, 1985;228(4701):815-22. Abstract Only.

Sugita et al., New insights into pathways for CD1-mediated antigen presentation. Curr Opin Immunol. Feb. 2004;16(1):90-5. Abstract Only.

Tupin et al., CDId-dependent activation of NKT cells aggravates atherosclerosis.J Exp Med. Feb. 2, 2004;199(3):417-22.

Van Den Elzen et al., Apolipoprotein-mediated pathways of lipid antigen presentation. Nature. Oct. 6, 2005;437(7060):906-10.

Van Den Elzen et al., Capture and specific delivery of exogenous lipid antigens by apolipoprotein E. Federation of Clinical Immunology Societies 2005 Meeting. Boston. May 11-16, 2005. Poster Abstract.

Van Den Elzen et al., Capture and specific delivery of exogenous lipid antigens by apolipoprotein E. Academy of Clinical Laboratory Physicians and Scientists. Pittsburgh. Jun. 9-11, 2005. Poster Abstract.

Winau et al., Saposin C is required for lipid presentation by human CD1b. Nat Immunol. Feb. 2004;5(2):169-74. Abstract Only.

Yamamoto et al., The human LDL receptor: a cysteine-rich protein with multiple Alu sequences in its mRNA. Cell. Nov. 1984;39(1):27-38. Abstract Only.

Zhou et al., Editing of CD1d-bound lipid antigens by endosomal lipid transfer proteins. Science. Jan. 23, 2004;303(5657):523-7, Abstract Only.

Fig. 4

APOLIPOPROTEIN E AS AN ADJUVANT FOR LIPID ANTIGENS

RELATED APPLICATIONS

This application claims priority under 35 U.S.C. §119 from U.S. provisional application Ser. No. 60/713,364, filed Sep. 2, 2005, entitled "Apolipoprotein E as an Adjuvant for Lipid Antigens", the entire contents of which are incorporated by reference herein.

GOVERNMENT SUPPORT

The present invention was supported in part by a grant from the United States National Institutes of Health Grant No. AI28973. The U.S. Government has rights in the invention.

FIELD OF THE INVENTION

The present invention is based upon the discovery that apolipoprotein E (apoE) can be used to promote an immune response against lipid antigens. Compositions containing apolipoprotein E and an antigenic lipid may be administered to animals to more efficiently produce an immune response against pathogenic microbes or against cancer cells. These compositions may also be administered to subjects in immunization protocols designed to provide protection against infectious diseases such as tuberculosis.

BACKGROUND OF THE INVENTION

There are two major types of immunity that protect people from infection: humoral immunity which is mediated by antibody-producing B-lymphocytes; and cell-based immunity which is mediated by T-lymphocytes. For many years, it was thought that peptides were the only important targets for T-cells. However, it has recently become apparent that T cells also recognize an array of lipids and glycolipids that are found on the membranes of altered mammalian cells (e.g., neoplastic cells) and microbial pathogens (such as the microorganism responsible for tuberculosis).

As with proteins, there are "antigen presenting cells" (APCs) that process lipids and display antigenic segments on their membrane surfaces. These antigenic segments are held in place by "CD1" proteins which, together with antigen, form a complex that is recognized by CD1-restricted T-cells including NKT (Brigl et al., *Annu. Rev. Immunol.* 22:817-90 (2004)). Upon binding to such a complex, the T-cells become activated and initiate an immune response by producing pro-inflammatory cytokines, stimulating antibody-producing B cells or directly killing the target APC. From a therapeutic standpoint, one advantage of the CD1 pathway of antigen presentation is that it is the same from person to person. Thus, in contrast to peptide antigens, an immune treatment that is based on lipid antigens should work for everyone.

Recently, saposins were shown to mediate an important step in antigen presentation by participating in the transfer of lipid antigens to CD1 molecules in lysosomes (Kang et al., *Nat. Immunol.* 5:175-81 (2004); Winau et al., *Nat. Immunol.,* 5:169-74 (2004); Zhou et al., *Science* 303-523-7 (2004)). However, apart from this, the mechanisms by which lipid antigens are delivered to APCs and transferred to CD1 are poorly understood. A better understanding of this process may lead to the development of improved vaccines and to new methods for treating cancer and autoimmune diseases.

SUMMARY OF THE INVENTION

The present invention is based upon the discovery that apolipoprotein E (apoE) promotes an immune response by facilitating the uptake of lipids by antigen presenting cells. Thus apoE may be used essentially as an adjuvant which, together with lipids or lipid fragments, is administered to a subject to, inter alia, boost immunity, including both T-cell mediated immunity and antibody production. The apoE/lipid compositions may be given to animals such as rabbits, sheep, goats, etc. to more efficiently produce immune responses against lipids found on microbes or cancer cells. The antibodies produced from this immune response can be used either in research or diagnostically, e.g., in assays for pathogens such as those responsible for tuberculosis or leprosy. The apoE/lipid compositions may also be used in immunization protocols in which a subject (e.g., a person, research animal, domestic animal or farm animal) is administered the lipid antigen to develop immunity against a particular disease.

It has also been discovered that it is the LDL receptor on antigen presenting cells that is responsible for recognizing apoE/lipid antigen complexes and which allows the uptake of antigen for presentation. Thus, receptor antagonists (i.e., compounds that block the interaction of apoE with the LDL receptor) or agents that block the binding of apoE to a particular lipid will inhibit uptake and will be useful to researchers in methods designed, for example, to examine the importance of lipid-based immunity in autoimmune diseases and in immune responses to infectious agents. One agent that appears to bind to apoE is heparin and it is believed that this compound may be used to either block the interaction of apoE with lipid or to block its interaction with the LDL receptor. Thus heparin at the same doses presently used in anticoagulant therapy may be administered to block the presentation of lipid antigens and may therefore be of value in the study or treatment of certain autoimmune diseases such as multiple sclerosis. In addition, apoE/lipid binding assays may be used to identify inhibitors (e.g., monoclonal antibodies) that can be used to block the uptake of specific lipid antigens.

In the first aspect, the invention is directed to a pharmaceutical composition in unit dose form that contains apolipoprotein E (preferably human apoE) and an antigenic lipid in a pharmaceutically acceptable liquid carrier. The term "antigenic lipid" refers to lipids which, when administered to a subject, induce an immune response. Typically, these lipids would be found on the surface of a disease-causing microorganism such as *M. tuberculosis* or *M. avium*. Alternatively, an antigenic lipid may be found on the surface of human cells after they have transformed to become cancerous but not prior to the time of such transformation. Examples of lipids that may be used in compositions include mycolic acid, glycosylated mycolates and glycosyl phosphoisoprenoids. Other specific examples include phosphoglycolipids, phosphatidylinositol mannosides or lipoarabinomannan. Numerous glycolipid antigens have been described on cancer cells that may be used, including gangliosides such as GD3. Also, it has recently been reported that the self glycolipid iGb3 is a natural self antigen that activates NKT cells, as does the synthetic glycolipid alpha-galactosyl ceramide. Examples of lipid antigens are described in U.S. Pat. Nos. 5,679,347, 5,853,737, 6,238,676 and 7,063,844.

The apolipoprotein E should typically be present in compositions in a molar ratio relative to antigenic lipid of between 0.1:1 and 100:1 and, preferably, the molar ratio of apoE/lipid antigen should be between 1:1 and 20:1. Together, the apoE and antigenic lipid should be present in compositions in an amount sufficient to induce an immune response when one or more unit doses of the pharmaceutical compositions are administered to a subject.

The invention further provides compositions comprising apoE and antigenic lipid, both of which or one of which is present in an isolated form. The molar ratio of apoE to antigenic lipid may vary from 0.1:1 to 100:1.

The term "unit dose form" refers to a single drug administration entity such as a tablet or capsule. However, since apoE is a protein and subject to degradation in the stomach of a patient, usually it will be necessary to administer it orally in an enterically coated dose form or, preferably, to administer compositions by injection. The "pharmaceutically acceptable liquid carrier" used in the unit dose forms should have all of the characteristics recognized in the art as being essential for such carriers. Thus, the liquid carrier should be sterile and non-toxic.

The pharmaceutical compositions described above may be included as part of a therapeutic package that is provided in a form that facilitates administration to subjects by injection. Thus, the pharmaceutical composition may be sold in a finished injection vial, ampoule or in a prefilled disposable syringe. The package may also include instructions for administering the pharmaceutical composition to subjects for immunization or to induce antibody production.

The invention also includes a method for improving pharmaceutical compositions that exist in unit dose form and which are designed for immunizing subjects using antigenic lipids. The method involves adding apoE to the composition to a final molar ratio relative to antigenic lipid of between 0.1:1 and 100:1, and preferably between 1:1 and 20:1. The improvement may be applied to compositions containing any of the lipids discussed above and involve compositions designed for use in either a research or clinical setting.

In another aspect, the invention encompasses methods of producing antibodies in a subject capable of such production by administering a pharmaceutical composition containing a lipid antigen and apoE. The "subject capable of antibody production" could be a human, domestic animal, farm animal, or research animal. Administration may be designed to provide immunity to the animal or it may be designed to induce antibody production for some other purpose. For example, antibodies may be generated in a laboratory setting for research purposes or antibodies may be produced that can be used in diagnostic assays performed clinically to identify the presence of infectious agents such as *M. tuberculosis* or *M. avium*.

An ability to inhibit the uptake of antigenic lipids by antigen presenting cells would be useful to researchers studying the importance of lipid antigens in autoimmune diseases and in the body's response to infectious agents such as infectious bacteria. Thus, methods of inhibition that are performed by either contacting the antigen presenting cell with an LDL receptor antagonist or by contacting the antigenic lipid with an agent that prevents it from binding to apoE are also part of the invention. The primary cells involved in taking up and presenting lipid antigens are dendritic cells or macrophages and it is contemplated that the main types of agents that will be used for specifically blocking interactions between apoE and lipid antigens will be monoclonal antibodies. In one embodiment, the agent is heparin or a heparin fragment.

Finally, the invention includes a method for determining whether a test compound is likely to be useful in inhibiting the uptake of an antigenic lipid by an antigen presenting cell. The method involves performing a binding assay between apoE and the antigenic lipid both in the presence and absence of the test compound. If the test compound blocks interaction between apoE and lipid, it should also be useful in preventing the recognition of lipid by antigen presenting cells and, ultimately, it should block an immune response to the lipid antigen.

BRIEF DESCRIPTION OF THE DRAWINGS

FIG. 1: Distribution and presentation of lipid antigens in human serum and dependence on apoE.

A) VLDL localization of CD1-restricted T cell activity. Sonicated GGC was incubated in human serum at 0.8 μ/ml for 1-6 hours at 37° C., and run on a Superose-6 column with PBS. 0.6 ml fractions were collected and assayed for T cell reactivity (solid line) by directly pulsing DC's, co-culturing with αGC-reactive T cells, and measuring IFNγ release in 16-24 hours by ELISA. The positions of VLDL, LDL and HDL (dashed line) were determined by standard calorimetric assays for cholesterol and triglyceride as described previously (Innis-Whitehouse et al., *J. Lipid Res.* 39:679-90 (1998)). Data are representative of six separate experiments.

B) Dependence of antigen reactivity upon apoE. Using the method described in (A), T cell stimulation by individual serum fractions (filled circles) was measured in the absence or presence of polyclonal blocking antibodies to apolipoprotein E (open circles) versus isotype-matched antibodies to apolipoprotein B (triangles) and apolipoprotein A-II (asterisks).

C) Depletion of apoE from serum diminishes GGC reactivity. One ml samples of human serum were depleted of apoE using an imunnoaffinity column as previously described (Tomiyasu et al., *Arterioscler. Thromb. Vasc. Biol.* 21:1494-500 (2001)). T cell reactivity to GGC was compared in 5% normal human serum, the same serum depleted of apoE, the apoE-depleted fraction plus added apoE (2.5 μg/ml) and the apoE positive fraction eluted from the column. Data are means of triplicate samples +/−SEM and are representative of four independent experiments using two separate apoE depletion columns and varying doses of antigen. Statistics reflect all doses in all experiments: *$p<0.001$, $p<0.001$, *$p<0.01$.

D) ApoE−/− mice and age-matched wild type controls were injected intravenously with 200 ng GGC, anti-CD3 (1.5 μg) or vehicle alone. Spleens and livers were harvested and TcRβ-positive, CD19-negative, CD1d tetramer positive cells analyzed for intracellular IFNγ production by flow cytometry. Results shown are for spleen, and similar results were seen for liver. Represents three separate experiments with 15 apoE−/− mice and 15 controls.

FIG. 2: ApoE binds lipid antigens and enhances CD1-dependent T cell responses.

A) ApoE-GGC binding. Freshly sonicated GGC (Free GGC) was either directly loaded on a heparin-sepharose column or pre-incubated with recombinant apoE for 10 minutes at room temperature before loading (GGC+apoE). ApoE was eluted from the column using 1 M NaCl. Fractions were assayed for antigenic activity as in FIG. 1. There was no difference in non-specific loss to the column. Data are representative of at least six separate experiments.

B) ApoE enhancement of GGC reactivity. Sonicated GGC was incubated with the indicated components in serum-free media with 4 mg/ml bovine serum albumin (BSA) as a carrier for 1-2 hours (or freshly sonicated) before pulsing DC and co-culturing with αGC reactive T cells in media supplemented with 2% human serum. IFNγ was measured in 16-24 hours by ELISA.

C) Dose-dependence of apoE. As in (B), αGC, GGC (100 ng/ml) or tetanus toxoid (TT, 10 μg/ml) was incubated with varying concentrations of apoE for 1 hour before pulsing DC and measuring T cell activation by IFNγ release (αGC-reactive clone, upper panel) or IL-4 release (TT-reactive clone, lower panel).

D) Enhancement of a CD1b dependent T cell response against foreign antigens. The mycobacterial derived antigen glucose monomycolate (GMM) was incubated with or without apoE in serum-free media with 4 mg/ml BSA and pulsed onto DC for 10 minutes, washed and cultured with the CD1b-restricted T cell line LDN5 in media supplemented with 5% human serum.

FIG. 3: Receptor-mediated uptake of apoE-bound lipid antigens.

A) ApoE enhances the efficiency of presentation of GGC. ApoB-loaded GGC (solid squares and striped bars) or sonicated free GGC (open triangles and open bars) was incubated with DC in serum-free media with 4 mg/ml BSA for the indicated times before washing and testing the ability to stimulate T cells as described in FIGS. 1 and 2. Upper panel: Dose response curve of GGC for 2 minute pulse. Lower panel: Various pulse times are shown for 50 ng/ml GGC.

B) The LDL receptor (LDL-R) is upregulated as monocytes differentiate into DC. Monocytes cultured in GM-CSF and IL-4 were harvested on the indicated days and LDL-R expression was determined by flow cytometry using biotinylated rabbit anti-LDL-R and streptavidin Alexa-488 compared to control (ctrl) stained with matched antibody and secondary reagent.

C) Free GGC or apoE-GGC was pulsed onto DC in the presence of increasing concentrations of apoB, and the subsequent activation of αGC reactive T cells was measured. There was no effect of apoB on PHA-stimulation of T cells. All data are representative of at least three experiments.

D) LDLR-/- and matched wild type controls were challenged intravenously with 200 ng GGC, 1.5 μg anti-CD3 or vehicle as described in FIG. 1D. Shown are results from spleen, with similar results in the liver. Represents two separate experiments with 10 LDLR-/- and 10 wild type mice.

Delivery of lipids to the endosomal system by receptor-mediated endocytosis via three possible mechanisms: 1) Secretion-capture: secreted (or recycled) apoE is relatively delipidated (Heeren et al., *J. Biol. Chem.* 278:14370-8 (2003)) and can capture lipid antigens or antigenic complexes. 2) Bystander acquisition: infected cells such as macrophages may rely on bystander DC to acquire shed antigens delivered by endogenously produced apoE. 3) Serum lipoproteins (VLDL in the case of GGC) serve as a likely depot of lipid antigens and may stimulate a response far from the source of the antigen.

DETAILED DESCRIPTION OF THE INVENTION

I. ApoE, LDL Receptors and Lipid Antigen

The apoE and lipid antigens which are used in the compositions described herein can be either chemically synthesized or purified using well established methods. Any form of apoE that is known in the art may be used in the compositions, but the most preferred form is human apoE. This protein is available commercially from several different sources including Alpha Diagnostic International (San Antonio, Tex.), EMD Bioscience (San Diego, Calif.) and Intracel Resources (Frederick, Md.). Alternatively, the protein can be chemically synthesized or recombinantly produced using known nucleotide and protein sequences (see GenBank accession nos. AF261279 and AF261279.1; Paik et al., *Proc. Natl. Acad. Sci. USA* 82:3445-9 (1985); and Nickerson et al., *Genome Res.* 10:1532-45 (2000)). Compositions may contain either full length lipids or portions of lipids designed to provoke an immune response. These compounds can be synthesized or purified using standard methods well known in the art.

ApoE and/or the antigenic lipid may be present in isolated form. As used herein, an isolated form is one that has been physically separated from the bodily and/or cellular components and molecules with which it would normally be associated in nature. For example, isolated apoE includes apoE from fractionated serum or recombinant apoE.

LDL receptors may be used in certain of the methods described herein. The human form of this receptor is preferred and is expressed on, for example, human dendritic cells. The complete nucleotide and amino acid sequences for the receptor have been reported (see GenBank accession nos. AAA56833 and AAA56833.1; Yamamoto et al., *Cell* 39:27-38 (1984); and Sudhof et al., *Science* 228:815-22 (1985)).

Certain aspects of the invention relate to the use of heparin, heparin fragments or heparin derivatives to inhibit apoE/antigen presentation to the immune system. Heparin is a sulfated polysaccharide which consists mainly of an alternating sequence of hexuronic acid and 2-amino-2-deoxy-D-glucose. Heparin, heparin fragments and heparin derivatives are described in U.S. Pat. Nos. 4,816,446, 5,039,529, 5,010,063, 6,326,476, 6,953,625 and 6,969,705.

Other aspects of the invention relate to the use of antibodies specific to apoE. Such antibodies are known in the art and are commercially available including for example D6E10 and E6D7 both of which are mouse antibodies that react with human apoE (available from Abcam). Anti-apoE antibodies may be monoclonal or polyclonal. They may be chimeric antibodies such as but not limited to humanized antibodies. These aspects of the invention may also use antibody fragments including but not limited to Fab, F(ab)$_2$, Fv, Fd, and single chain antibodies, all of which are known in the art.

II. Pharmaceutical Compositions and Therapeutic Packages

Pharmaceutical compositions containing apoE and antigenic lipid are described more fully in section V below. In general, these compositions will be designed for administration to a subject by intramuscular, intravenous or subcutaneous injection. Solutions containing apoE and lipid can be prepared using any of the carriers and excipients that are known in the art to be suitable for this purpose. Examples of suitable parenteral compositions would include those containing sterile isotonic saline, water, 1,3-butanediol, ethanol, 1,2-propylene glycol, polyglycols mixed with water, etc. In all cases, formulations may be prepared using standard methods (see, e.g., *Remington's Pharmaceutical Sciences*, 16$^{th}$ ed., Easton, Pa. (1980)). If desired, additional agents, such as preservatives, may be added to solutions or preparations may be sparged with non-oxidizing gas, e.g., nitrogen and/or $CO_2$. Antioxidants may also be added to compositions if desired.

The pharmaceutical compositions may, if desired, be included as part of a therapeutic package. Such packages may contain the pharmaceutical composition in ampoules or vials for injection or the compositions may be provided in prefilled disposable syringes. Syringes should generally only contain a single dose which will, in most instances consist of between 0.5 and 5.0 ml. Syringes, vials or ampoules will typically be enclosed in a sealed package which may, optionally, be treated to remove oxygen. Standard methods for filling and packing syringes, vials and ampoules are well known in the art and may be used in conjunction with the present invention. In addition, therapeutic packages will usually include instructions describing how compositions may be administered to either generate the production of antibodies or to immunize a subject.

III. Antibodies to Lipids

The present invention includes methods in which the interaction between apoE and a specific lipid antigen is blocked. These methods may be used by researchers examining the importance of the lipid as an antigen in protecting against a disease or bacterial infection. Agents blocking this interaction can be identified using the binding assays discussed below. In general, it is believed that these agents will be monoclonal antibodies that bind with specificity to the lipid antigen. For the purposes of the present invention, antibodies that "bind with specificity" are defined as those that have at least a one hundred-fold greater affinity for the selected lipid than for any other lipid or protein. The process for producing such antibodies may involve either injecting the lipid itself into an appropriate animal or, alternatively, injecting short segments corresponding to different regions of the lipid.

Regions that are unique to specific lipids should generally be chosen for injection. Methods for making and detecting antibodies are well known to those of skill in the art as evidenced by standard reference works such as: Harlow et al., *Antibodies, A Laboratory Manual*, Cold Spring Harbor Laboratory, NY (1988); Klein, *Immunology: The Science of Self-Nonself Discrimination* (1982); Kennett et al., *Monoclonal Antibodies and Hybridomas: A New Dimension in Biological Analyses* (1980); and Campbell, "Monoclonal Antibody Technology," in *Laboratory Techniques in Biochemistry and Molecular Biology* (1984). "Antibody", as used herein, is meant to include intact molecules as well as fragments which retain their ability to bind to antigen. Monoclonal antibodies can be prepared using hybridoma technology (Kohler et al., *Nature*, 256:495 (1975); Hammerling et al., in: *Monoclonal Antibodies and T-Cell Hybridomas*, Elsevier, M. Y., pp. 563-681 (1981)). In general, this technology involves immunizing an animal, usually a mouse, with either intact lipid or a fragment derived from the lipid. The splenocytes of the immunized animals are extracted and fused with suitable myeloma cells, e.g., $SP_2O$ cells. After fusion, the resulting hybridoma cells are selectively maintained in HAT medium and then cloned by limiting dilution (Wands et al., *Gastroenterology* 80:225-32 (1981)). The cells obtained through such selection are then assayed to identify clones which secrete antibodies capable of binding to lipid and then for their ability to block the binding of apoE to lipid.

IV. Binding Assays

Binding assays are of importance in two different aspects of the present invention. First, they provide a way to identify LDL receptor antagonists. These antagonists may be used in a laboratory setting to block the uptake of lipid antigen by cells and to thereby help assess the importance of mechanism to an organism, e.g., in protecting against infection. In radio-ligand binding assays, a source of the LDL receptor, e.g., human dendritic cells, is incubated together with apoE (preferably bound to an antigenic lipid) and with a test compound, i.e., a compound being examined for its ability to block binding. The assay may be performed either with intact cells or with membranes prepared from the cells (see e.g., Wang et al., *Proc. Natl. Acad. Sci. U.S.A.* 90:10230-4 (1993)).

The membranes, or cells, are incubated with labeled ligand (i.e., either apoE or apoE/lipid complex) and with a preparation of the test compound. After binding is complete, receptor is separated from the solution containing ligand and test compound, e.g. by filtration, and the amount of binding that has occurred is determined. Preferably, the ligand used is detectably labeled with a radioisotope such as $^{125}I$. However, if desired, fluorescent or chemiluminescent labels can be used instead. Among the most commonly used fluorescent labeling compounds are fluorescein, isothiocynate, rhodamine, phycoerythrin, phycocyanin, allophycocyanin, o-phthaldehyde and fluorescamine. Useful chemiluminescent compounds include luminol, isoluminol, theromatic acridinium ester, imidazole, acridinium salt, and oxalate ester. Any of these agents can be used to produce a ligand suitable for use in the assay.

Nonspecific binding may be determined by carrying out the binding reaction in the presence of a large excess of unlabeled ligand. For example, labeled ligand may be incubated with receptor and test compound in the presence of a thousand-fold excess of unlabeled ligand. Nonspecific binding should be subtracted from total binding, i.e., binding in the absence of unlabeled ligand, to arrive at the specific binding for each sample tested. Other steps such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced receptor binding.

In performing binding assays, care must be taken to avoid artifacts which may make it appear that a test compound is interacting with the LDL receptor when, in fact, binding is being inhibited by some other mechanism. For example, the compound being tested should be in a buffer which does not itself substantially inhibit binding to receptor and should, preferably, be tested at several different concentrations. Preparations of test compound should also be examined for proteolytic activity and it is desirable that antiproteases be included in assays. Finally, it is highly desirable that compounds identified as displacing binding to the LDL receptor be reexamined in a concentration range sufficient to perform a Scatchard analysis of the results. This type of analysis is well known in the art and can be used for determining the affinity of test compounds for receptor (see e.g., Ausubel et al., *Current Protocols in Molecular Biology*, 11.2.1-11.2.19 (1993); *Laboratory Techniques in Biochemistry and Molecular Biology*, Work et al., ed., NY, (1978) etc.). Computer programs may be used to help in the analysis of results (see e.g., Munson, P., *Methods Enzymol.* 92:543-77 (1983); McPherson, G. A., *Kinetic, EBDA Ligand*, Lowry-A Collection of Radioligand Binding Analysis Programs, Elsevier-Biosoft, U.K. (1985)).

Binding assays analogous to those described above may also be performed to identify compounds (or antibodies) blocking the binding of apoE to a lipid antigen. In these assays, either the lipid or the apoE may be labeled with the other, nonlabeled compound being immobilized, e.g., on a multiwell plate. Binding assays may then be carried out in the presence of various concentrations of a test compound. If a compound is determined to inhibit binding, its specificity for the particular lipid used in the assay can be determined by repeating the assay with a variety of different lipids. Many variations on these types of assays are known in the art and can be used in conjunction with the present invention.

V. Vaccines

The invention includes vaccines containing apoE and antigenic lipid that can be given to a subject (e.g., a human, primate, horse, sheep, rabbit, swine, goat, cow, dog or cat) to immunize them against a disease or condition. For present purposes, the term "vaccine" includes both compositions given to human or animal to immunize them and compositions given to an animal to induce the production of antibodies that will be isolated and subsequently used, e.g., for research or diagnostic purposes. Typically, a vaccine will contain between 0.1 and 1000 μg of lipid in a volume of between about 0.5 and 5 ml. The lipid should be part of a pharmaceutically acceptable composition, i.e., the composition should be sterile, non-toxic and, preferably, isotonic with the blood of the recipient subject.

ApoE should be included in the pharmaceutically acceptable composition at a molar ratio relative to lipid of between 0.1:1 (i.e., 0.1 moles of apoE for each mole of lipid) and 100:1, and preferably at between 1:1 and 20:1. The molar ratios may be 0.5:1, 2:1, 3:1, 4:1, 5:1, 10:1, 15:1, 25:1, 50:1, 75:1, or any other ratio that falls within the ranges set forth herein as if explicitly recited.

It is to be understood that apoE may be formulated separated or together with the antigenic lipid. Similarly, apoE and the antigenic lipid, if formulated separately may be administered by the same route (e.g., by combining the two formulations just prior to administration to a subject), or they may be administered by different routes.

Formulation may take place using standard methods such as those described in *Remington's Pharmaceutical Sciences* (Mack Publishing Co., Easton, Pa., 16$^{th}$ ed. (1982)). Besides apoE and lipid, vaccines will include a pharmaceutically acceptable carrier. Examples of suitable carriers include sodium phosphate-buffered saline (pH 7.4). Ringer's solution, water, mineral oil, water in oil suspensions or emulsions, organic solvents, etc. Other buffering agents that may be used include acetate buffers, citrate buffers, borate buffers and bicarbonate buffers. Preservatives that may be used in compositions include benzalkonium chloride (0.003-0.03% w/v); chlorobutanol (0.3-0.9% w/v); parabens (0.01-0.25% w/v) and thimerosal (0.004-0.02% w/v). The apoE will serve as an adjuvant for the lipid but, if desired, other adjuvants may be added to compositions as well. The term "adjuvant" is intended to include any substance which is incorporated into or administered with (e.g., prior to, simultaneously with, or after) the antigenic lipid and which increases or potentiates the immune response in the recipient subject. Adjuvants that are typically used include aluminum compounds, and Freund's complete or incomplete adjuvant.

Vaccines will generally be designed for parenteral administration, although the present invention is compatible with other forms of administration as well. Immunization procedures will typically involve several inoculations with vaccine (e.g., three inoculations) separated by intervals of 3 to 10 weeks. Procedures for optimizing inoculation schedules and the other parameters associated with immunization are well known in the art.

EXAMPLES

In the present example, the pathway mediating exogenous lipid antigen delivery by apolipoproteins to achieve antigen presentation by CD1 is defined. ApoE plays a major role in the delivery of model serum-borne lipid antigens and further can transfer microbial lipids from infected macrophages to uninfected bystander APCs. ApoE-lipid antigen complexes are internalized by receptor mediated uptake resulting in rapid and efficient antigen delivery to endosomal lipid antigen loading compartments enabling CD1 restricted T cell activation. Thus, the immune system has co-opted an important component of lipid metabolism to develop immune responses to lipid antigens.

Studies Using Serum

Serum, lymph, and interstitial fluid represent the physiological contexts in which extracellular lipid antigens are encountered by CD1+ antigen presenting cells in vivo. Lipid-transport particles termed lipoproteins are a major constituent of these extracellular compartments. To assess their contribution to the immune recognition of lipids, an in vitro system was used in which human dendritic cells (DC) were cultured with CD1 presented lipid antigens in human serum to measure their uptake and stimulatory capacity for T cells. A model CD1d presented glycolipid, galactosyl(α1-2)galactosyl ceramide (GGC), was used in these studies because this antigen strictly requires uptake and delivery to lysosomes where it is converted to the active antigenic form, α-galactosyl ceramide (αGC) (Prigozy et al., *Science* 291:664-7 (2001)).

GGC was allowed to distribute into human serum at 37° C. for 1-6 hours, after which the various serum fractions were separated on a Superose-6 column to resolve the major lipoprotein components of serum, namely very low density, low density and high density lipoproteins (VLDL, LDL and HDL). The fractions were then assayed for their ability to stimulate αGC-reactive, CD1d-dependent NKT cells.

Figure 1A:
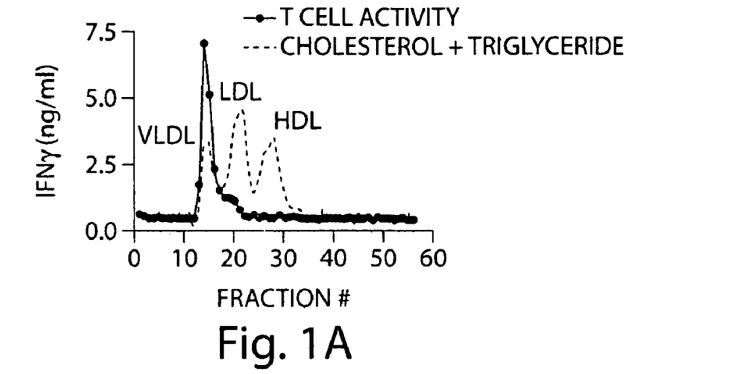
Figure 1B:
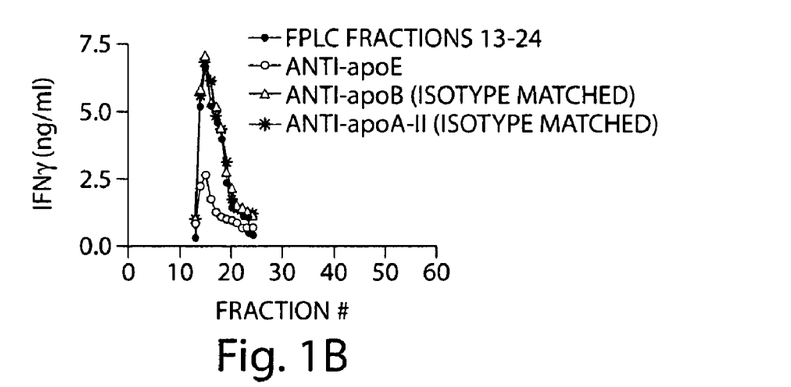

It was found that the antigenic activity of GGC distributed almost entirely in the VLDL fraction of human serum (FIG. 1A). VLDL is a complex of lipids and apolipoproteins, including apolipoprotein B (apoB) and apoE, which independently participate in receptor-mediated uptake into cells (Krul et al., *J. Clin. Invest.* 75:361-9 (1985); Sacks et al., *Vas. Med.* 1:9-18 (1996)). Only antibodies against apoE effectively blocked the VLDL-mediated T cell activity (70-80% inhibition), compared to isotype-matched antibodies against apoB or apoA-II (FIG. 1B). This effect was specific for VLDL-bound GGC, since there was no effect of anti-apoE blocking antibodies on the T cell response when sonicated free GGC was co-cultured with DC in serum-free media, or when T cells were stimulated with phytohemagglutinin (PHA), a control polyclonal T cell activator. Thus, the exogenously supplied lipid antigen GGC, binds in the VLDL fraction of serum, and is acquired by DC in an apoE-dependent manner, processed, and then presented to T cells.

Figure 1C:
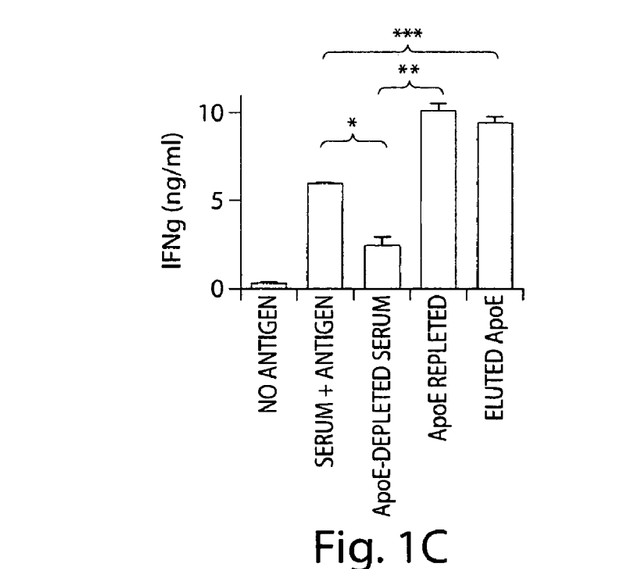

To demonstrate the importance of apoE in serum in the uptake and presentation of this lipid antigen, apoE was depleted from human serum using an immunoaffinity column (Tomiyasu et al., *Arterioscler. Thromb. Vasc. Biol.* 21:1494-500 (2001)). ApoE-depleted serum incubated with GGC had a significantly reduced capacity to stimulate T cells, compared to normal serum, and the presenting capacity was recovered by adding back purified apoE (FIG. 1C). Further, the apoE-positive fraction of serum had an enhanced stimulatory capacity compared to serum alone. These results suggest that apoE is the major factor in serum mediating the presentation of GGC to CD1d-reactive T cells.

Experiments Using ApoE-Deficient Mice

Figure 1D:
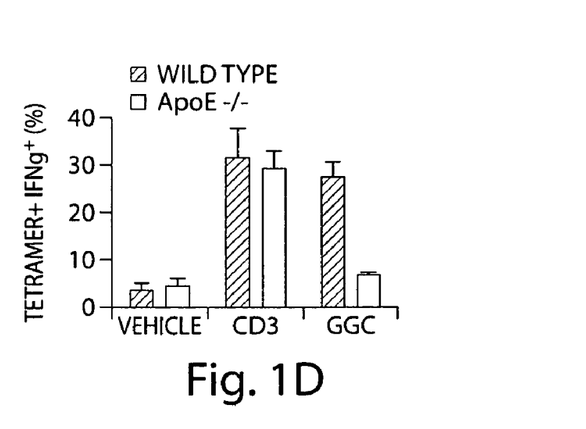

To assess the importance of apoE in the presentation of lipid antigens in vivo, the CD1d-restricted response to GGC in apoE-deficient mice was analyzed. Although there were comparable numbers to αGC-reactive NKT cells in apoE knockouts and wild type controls, the response to intravenously administered GGC was drastically reduced in the apoE-deficient mice (FIG. 1D). This was not due to a non-specific deficit of T cell reactivity, since intravenous administration of anti-CD3 antibodies activated αGC reactive T cells similarly in both apoE-deficient mice and controls. Thus, apoE plays a crucial role in the in vivo presentation of an exogenous lipid antigen. It has been shown by others, however, that much higher doses of αGC can still activate NKT cells in apoE-deficient mice (Major et al., *Arterioscler. Thromb. Vasc. Biol.* 24:2351-7 (2004); Tupin et al., *J. Exp. Med.* 199:417-22 (2004)), thus indicating that alternative pathways of exogenous lipid presentation also exist.

Production of ApoE by DC and Macrophages

In addition to its role in serum, apoE is known to be secreted locally in tissues by macrophages and can account for 10% of all newly synthesized protein. It has also been reported that apoE is coordinately up-regulated with CD1 molecules in microarray experiments in human DC (Chaussabel et al., *Blood* 102:672-81 (2003); Le Naour et al., *J. Biol. Chem.* 276:17920-31 (2001)), further suggesting that apoE might be involved in lipid antigen acquisition and delivery to APCs. In the present study, it was confirmed that apoE is abundantly produced by both DC and macrophages, as apoE accumulated in supernatants at concentrations up to 10 μg/ml in culture. Thus, by locally producing apoE in their environment, DC or macrophages may be able to promote the capture and presentation of lipid antigens to T cells.

Binding of ApoE to Antigen

Figure 2A:
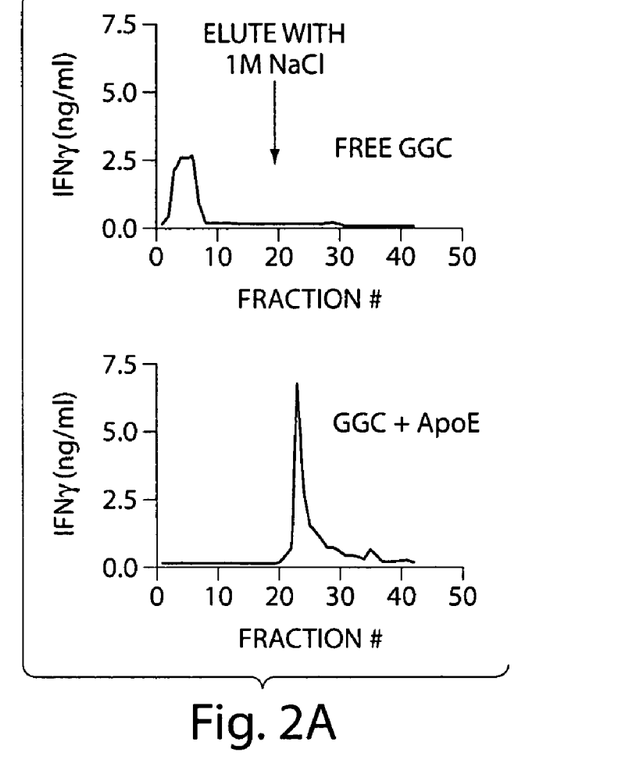

To directly examine the ability of apoE to bind antigens such as GGC, antigens were incubated with apoE, and then free separated from bound using a heparin affinity column. Whereas free lipid readily passed through the column (FIG. 2A, upper panel), apoE bound to the column with high affinity. After a 10 minute incubation of apoE with GGC at room temperature, all detectable lipid antigen remained bound to apoE, was retained by the column, and could be eluted with NaCl (FIG. 2A, lower panel). Even in the presence of a 500-fold excess of albumin, which itself can nonspecifically bind lipids, greater than 95% of the GGC still bound to apoE. Thus, apoE binds efficiently to a model CD1 presented lipid antigen.

Figure 2B:
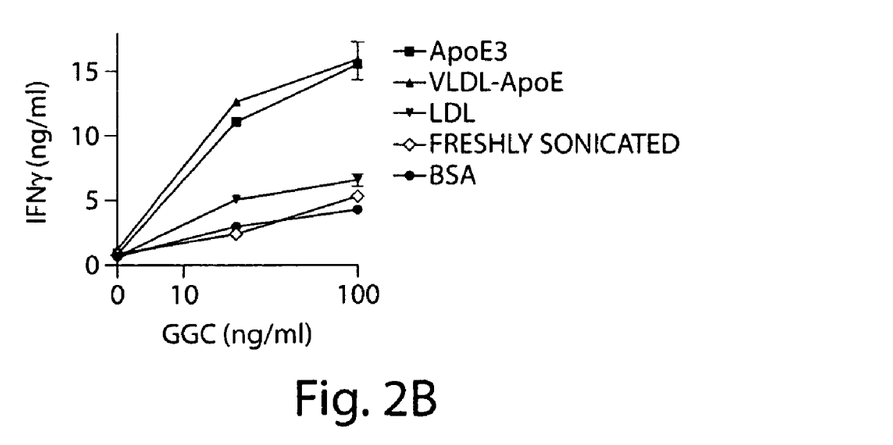
Figure 2C:
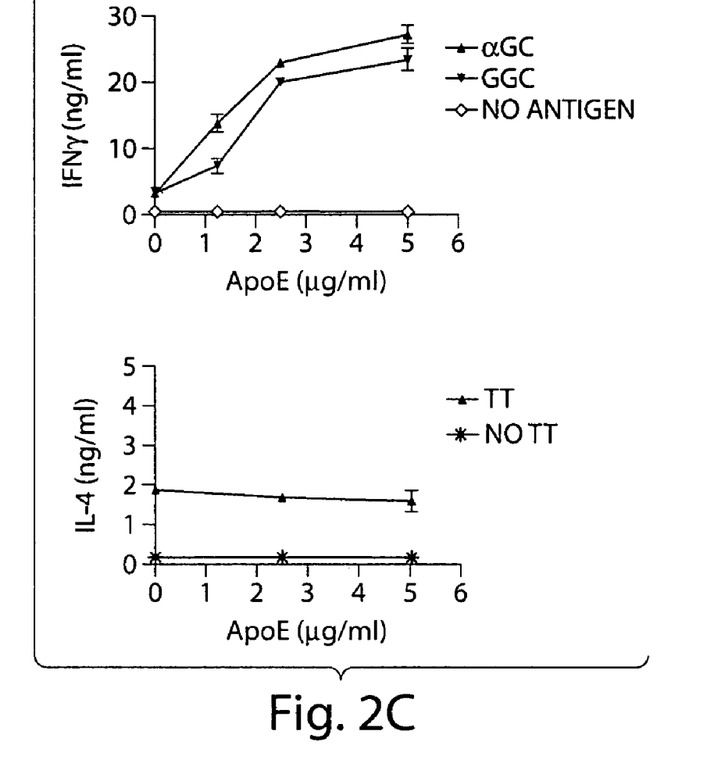

Next, experiments were performed to determine whether the delivery of lipid antigens bound to apoE enhances CD1-restricted T cell responses when compared to free lipid antigen. On a molar basis, the antigenic potency for T cells of apoE-bound GGC recovered from the heparin affinity column was significantly greater than free GGC (FIG. 2A). This was directly confirmed in experiments showing that the antigenic potency of GGC incubated with VLDL-derived apoE or recombinant apoE was increased almost 50-fold compared to freshly sonicated free GGC or GGC delivered with other lipoprotein or serum fractions such as HDL, LDL or albumin (FIG. 2B). The effect was specific for lipid-dependent T cell responses since there was no effect of apoE on a MHC class II restricted response to tetanus toxoid, an exogenous protein antigen also requiring uptake and processing in endocytic compartments of DC (FIG. 2C). In addition, apoE did not non-specifically activate T cells or DC since increasing the concentration of apoE had no effect on control T cell stimulators, such as CD3, PHA or PMA/ionomycin.

Studies with Microbial Antigens

Figure 2D:
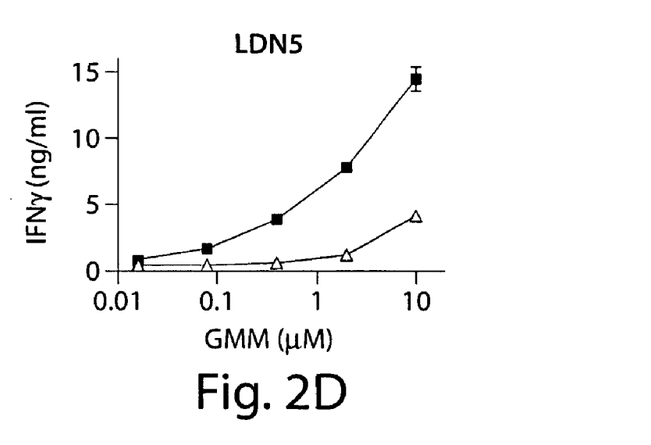

Given the known affinity for apoE for a wide variety of lipid classes, it seemed likely that binding and delivery of lipid antigens would apply to many CD1 presented lipid antigens. Thus, experiments were performed examining the T cell response to naturally occurring microbial lipid antigens presented by DC by CD1b and CD1c in the presence or absence of apoE. Glucose monomycolate (GMM) and mycolic acid were both more efficient at inducing CD1b restricted T cell activation when complexed with apoE (FIG. 2D). Similarly, the CD1c presented manosyl-phosphomycoketide (MPM) complexed with apoE was significantly more efficient at T cell stimulation than without apoE. Together, these results establish that apoE specifically enhances T cell responses to a variety of CD1-presented lipid antigens for multiple CD1 isoforms.

Effect of ApoE on Rapidity of Lipid Antigen Uptake

Figure 3A:
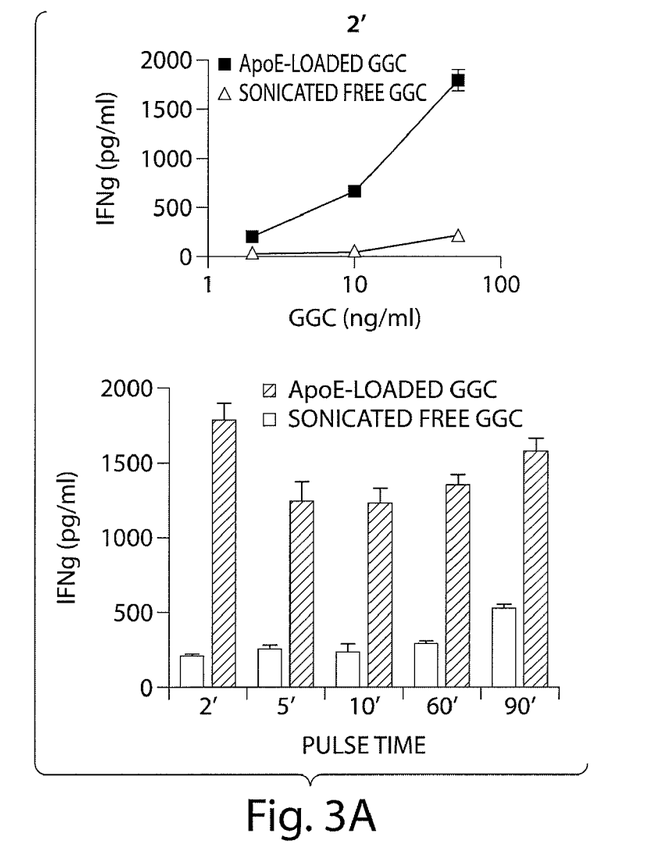

To determine the rapidity and efficiency of lipid uptake into DC, free lipid antigen or apoE-bound lipid antigen was used to pulse DC for varying times before washing the cells and assaying their subsequent ability to present antigen to T cells. Strikingly, apoE delivered GGC achieved maximal stimulation of T cells following a 2 minute exposure to DC, whereas free lipid in media alone required 4-6 hours to achieve its maximal stimulation, which still only reached 48% (+/−11%) of that achieved in 2 minutes with apoE (see FIG. 3A). This markedly enhanced rapidity and efficiency of uptake of the antigen is consistent with the difference between receptor-mediated endocytosis (apoE-delivered lipid) and macropinocytosis.

Studies on ApoE Receptors Mediating Lipid Antigen Uptake by DC

Figure 3B:
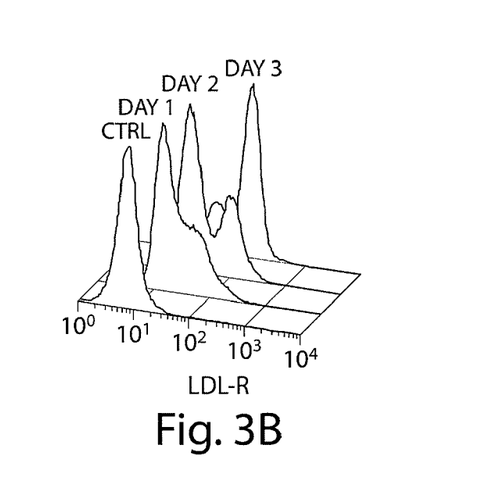

Flow cytometric analysis showed cell surface expression of LRP and LDL-R (two cell surface receptors known to take up apoE) on DC, the latter being markedly up-regulated during differentiation of monocytes to DC (FIG. 3B). To determine the roles of these cell surface receptors in the uptake of apoE-bound lipid, complementary approaches were taken. First, a comparison was made between the ability of ApoE3 (the most common human variant) and ApoE2 (a variant with a single amino acid change that diminishes binding to the LDL-R) to mediate lipid antigen uptake in DC. Compared to ApoE3, ApoE2 had just 40-47% the capacity to enhance the CD1d-dependent response. This suggests that the LDL-R plays a significant role in uptake of ApoE-antigen complexes. Furthermore, these results rule out the possibility that ApoE merely acts to "solubilize" the lipid antigen, allowing enhanced uptake via non-specific macropinocytosis.

Figure 3C:
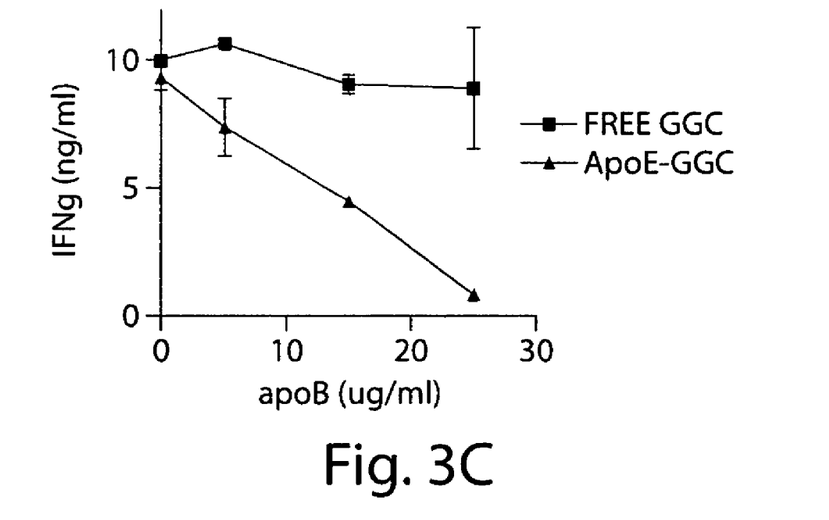

In a second approach, advantage was taken of the fact that apoB, the primary component of LDL, also binds to the LDL-R and can serve as a competitive ligand, while not binding LRP (Beisiegel et al., *Nature* 341:162-4 (1989)). DC pulsed with apo-GGC in the presence of increasing amounts of apoB exhibited a dose-dependent diminution of antigen presentation (FIG. 3C). As controls, increasing amounts of apoB had no effect on the dose response to free GGC (FIG. 3C) or on the PHA induced T cell response. The inhibition by apoB was thus specific for apoE mediated uptake and presentation, and further implicated the role of the LDL-R in uptake.

Figure 3D:
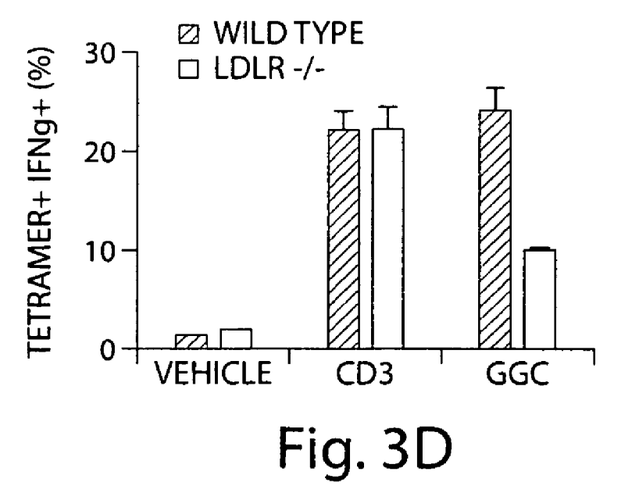

Finally, the response to GGC in LDL-R deficient mice was examined. Compared to wild type controls, LDL-R knockouts had a greatly diminished response to antigen while responding similarly to non-specific stimulation by anti-CD3 (FIG. 3D). Thus, it was concluded that the LDL-R plays a major role in the uptake of apoE-lipid antigen complexes and presentation by CD1.

Effect of ApoE on Delivery of Lipid to CD1 Antigen Loading Compartments

A fluorescent lipid probe, 1,1'-dioctadecyl-3,3,3',3'-tetramethylindocarbocyanine perchlorate (DiI) was used to directly visualize the delivery of free lipids versus apoE-bound lipids. This molecule resembles CD1-presented lipid antigens in having two 18-carbon fatty acyl chains, and a distinct headgroup, in this case giving it fluorescent properties allowing visualization within cells (Barak et al., *J. Cell Biol.* 90:595-604 (1981)). The intracellular fate of DiI delivered as ApoE-bound DiI was compared to free DiI by confocal microscopy in dendritic cells. ApoE-delivered DiI was found to result in rapid (5 minute) uptake in a punctuate endosomal pattern, co-localizing with the early endosomal marker transferrin. Freshly sonicated free DiI also rapidly entered dendritic cells, but distributed in an apparent plasma membrane distribution with very little endosomal localization. Thus, receptor mediated endocytosis of apoE concentrates lipid molecules rapidly in the endosomal system.

ApoE Mediated Lipid Antigen Transfer During Infection

Experiments were performed to visualize the apoE mediated transfer of exogenous lipid antigens in the setting of an infection. Macrophages are the host cells during infection by mycobacterium tuberculosis (Mtb), harboring the bacterium while being incapable of presenting lipid antigens via CD1a, b or c. Thus, it was hypothesized that lipid antigens may be transferred to uninfected CD1-positive DC to enable antigen presentation. Since macrophages abundantly produce apoE, these cells were infected in culture with live Mtb labeled with a fluorescent dye to tag mycobacterial surface glycolipids (see Beatty et al., *Traffic* 1:235-47 (2000)). The infected human macrophages were washed and cultured for 2-3 days after which secreted apoE was isolated with an immunoaffinity column. Remarkably, the apoE fraction contained abundant fluorescently labeled bacterial glycolipid, as evidenced by a rapid (15 minute) uptake into DC accumulating in a punctuate endosomal pattern completely colocalizing with staining for apoE, and partially coinciding with CD1b. Thus, apoE produced by infected macrophages transfers glycolipid antigens to uninfected "bystander" DC.

CONCLUSION

The experiments described above outline an exogenous pathway for lipid antigen presentation mediated by apoE through receptor mediated endocytosis. The exogenous pathway results in rapid uptake into DC with specific delivery to endosomal compartments resulting in markedly enhanced T cell stimulation. In vivo, the ability of bystander APC to pick up microbial antigens from the extracellular fluid may be essential for effective immunity when infected cells cannot themselves present antigen.

Figure 4:
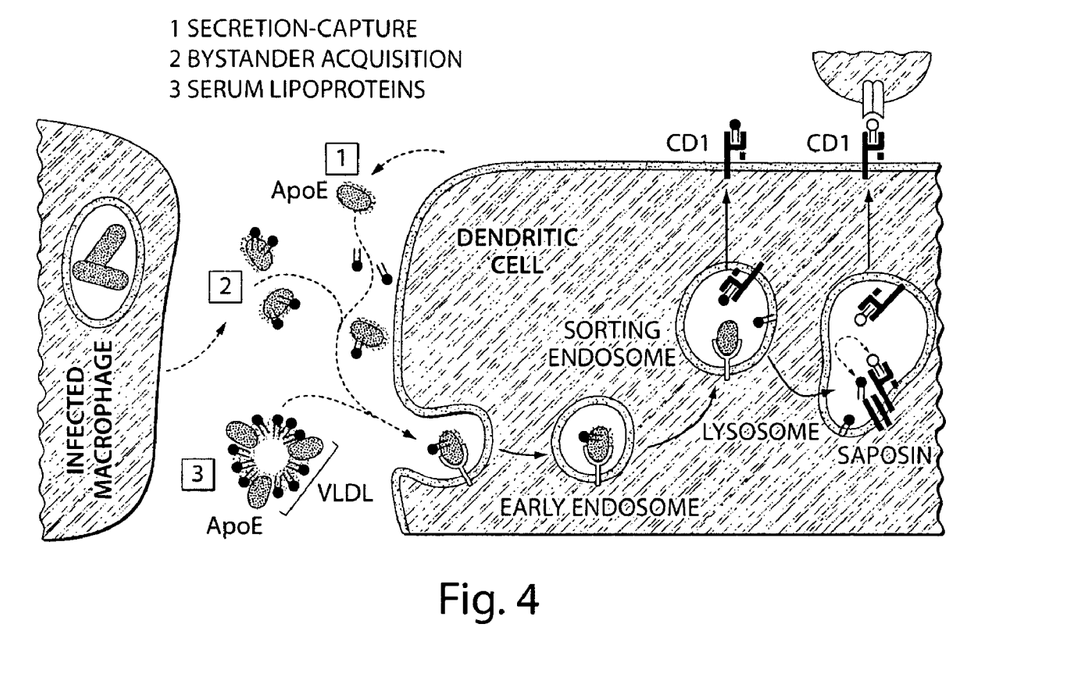
FIG. 4: Exogenous pathways for lipid antigen presentation mediated by apoE.

Based on the above studies, we propose that ApoE readily binds exogenous lipid antigens and efficiently targets them for receptor-mediated uptake by DC either in the infected tissue or in distant lymphoid organs to stimulate systemic immune responses. This may occur by secretion and capture of apoE-lipid antigen complexes in the local milieu or by apoE-VLDL lipid antigen complexes acquired from the circulation or tissue fluid (FIG. 4).

In addition to foreign lipids, apolipoproteins may also be important in providing a pathway for delivery of self-lipid antigens and contribute to inflammatory diseases such as multiple sclerosis or atherosclerosis where both apoE and CD1 have been independently implicated. Thus, the exogenous lipid antigen delivery pathway mediated by apolipoproteins has important implications for microbial immunity, autoimmunity and atherosclerosis.

EQUIVALENTS

All references, including patents, cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

The invention claimed is:

1. A method of inducing the production of antibodies against an antigenic lipid, comprising administering to a subject capable of antibody production a composition comprising:
   a) said antigenic lipid; and
   b) apolipoprotein E in an amount that, together with said antigenic lipid, is sufficient to induce production of said antibodies.

* * * * *

UNITED STATES PATENT AND TRADEMARK OFFICE
CERTIFICATE OF CORRECTION

| | |
|---|---|
| PATENT NO. | : 7,608,246 B2 |
| APPLICATION NO. | : 11/516017 |
| DATED | : October 27, 2009 |
| INVENTOR(S) | : Peter van den Elzen et al. |

Page 1 of 1

It is certified that error appears in the above-identified patent and that said Letters Patent is hereby corrected as shown below:

In the Specification:

At column 1 line 15, delete the paragraph under Government Support and replace with --This invention was made with Government support under Grant Nos. AI063428 and AI028973 awarded by the Public Health Service/National Institutes of Health. The Government has certain rights in this invention.--

Signed and Sealed this

Fifteenth Day of June, 2010

David J. Kappos
*Director of the United States Patent and Trademark Office*